United States Patent [19]
Franke et al.

[11] Patent Number: 5,972,633
[45] Date of Patent: Oct. 26, 1999

[54] ANTIBODIES AGAINST HEART MUSCLE ACTIN

[75] Inventors: Werner Wilhelm Franke; Sabine Stumpp, both of Heidelberg; Sabine Stehr, Malsch, all of Germany

[73] Assignee: Progen Biotechnik GmbH, Heidelberg, Germany

[21] Appl. No.: 08/930,695

[22] PCT Filed: Apr. 9, 1996

[86] PCT No.: PCT/DE96/00620

§ 371 Date: Jan. 14, 1998

§ 102(e) Date: Jan. 14, 1998

[87] PCT Pub. No.: WO96/32417

PCT Pub. Date: Oct. 17, 1996

[30] Foreign Application Priority Data

Apr. 10, 1995 [DE] Germany .......................... 195 13 595

[51] Int. Cl.[6] .................... G01N 33/53; G01N 33/542; C12Q 1/70; A61K 38/00
[52] U.S. Cl. .................... 435/7.92; 435/5; 435/7.1; 435/7.9; 530/300; 530/328; 530/344
[58] Field of Search ............... 435/7.92, 5, 7.1, 435/7.9; 530/300, 328, 344

[56] References Cited

PUBLICATIONS

Aranega, et al: Circulating alpha–actin protein in acute myocardial infaction: Int. J. Car.: Bd. 38, Nr. 1: pp. 49–55, Jan. 1993.

Hanin, et al. : Production of oligoclonal antibodies . . . : Pep. Res. : vol. 2, No. 6 :pp. 367–372, 1989.

International Journal of Cardiology, Bd. 38, Nr. 1, Jan. 1993, Amsterdam, NL, Seiten 49–55, XP00578319, A.E. Aranega et al, "Circulating Alpha–Actin Protein In Acute Myocardial Infarction".

Journal of Molecular and Cellular Cardiology, Bd. 25, Nr. 1, Jan. 1993, London, GB, Seiten 15–22, XP000578297, A.E. Aranega et al, "Circulating Alpha–Actin In Angina Pectoris".

Peptide Research, Bd. 2, Nr. 6, Nov. 1989, Natrick, GB, Seiten 367–372, XP002010880, V. Hanin et al, "Production of Oligoclonal Antibodies Directed to the N–Terminal of Smooth Muscle Alpha Actin Using Peptidyl–Polyacrylic Resins as Direct Immunogens".

"Sigma Immuno Chemicals, 1992 Katalog", 1992, Sigma Chemie GmbH, Deisenhofen, DE, XP002010881.

*Primary Examiner*—Frank C. Eisenschenk
*Assistant Examiner*—Brett Nelson
*Attorney, Agent, or Firm*—Burns, Doane, Swecker & Mathis, L.L.P.

[57] ABSTRACT

The present invention relates to antibodies against heart muscle actin, processes for the production of such antibodies and their use.

9 Claims, 1 Drawing Sheet

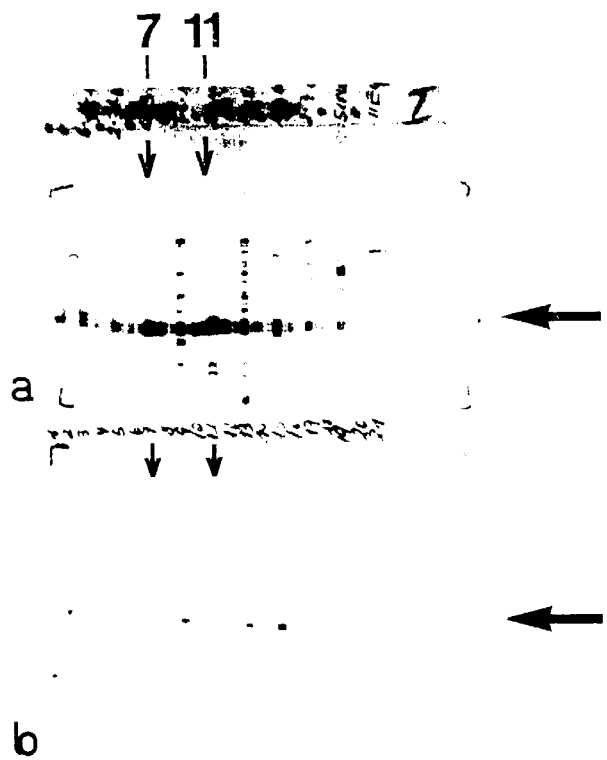
Figure
Western blot: Specific reaction of antibodies ACC 2208 and ACC 2209 according to the invention with heart muscle actin

SEQUENCE LISTING

<160> NUMBER OF SEQ ID NOS: 1

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: n-terminal
      peptide from heart muscle actin

<400> SEQUENCE: 1

Asp Asp Glu Glu Thr Thr Ala Leu Val Cys
1               5                   10

ANTIBODIES AGAINST HEART MUSCLE ACTIN

This application is a continuation of PCT/DE96/00620 filed Apr. 9, 1996.

The present invention relates to antibodies against heart muscle actin, processes for the production thereof and their use.

Processes are known for detecting a cardiac infarct by determining the heart muscle-specific creatine phosphokinase and by determining the serum-lactate dehydrogenase, respectively. However, the former determination cannot be made until 3 hours following a cardiac infarct. Also, only a maximum of 50% of the creatine phosphokinase is present after one day. Furthermore, the serum-lactate dehydrogenase is not a heart-specific enzyme. Thus, the above determinations are only suitable in a limited fashion for detecting a cardiac infarct or another lesion of the heart muscle.

Therefore, it is the object of the present invention to provide a product by which a cardiac infarct or another lesion of the heart muscle can be detected specifically and reliably.

According to the invention this is achieved by antibodies which are directed against heart muscle actin.

It follows from applicant's experiments that in the case of cardiac infarct heart muscle actin is released. This actin differs as regards few amino acids from the actin of the sceletal muscle and that of the smooth muscles, respectively (cf. Vandekerckhove, J. and Weber, K., Differentiation 14 (1979), pp. 123–133). According to the invention these differences are used to direct antibodies against heart muscle actin.

Such antibodies may be polyclonal or monoclonal, monoclonal antibodies being preferred. The antibodies may have been obtained from any animal or human being, rabbits being preferred for polyclonal antibodies and mice being preferred for monoclonal antibodies.

In addition, the antibodies may be synthetic, portions which are not necessary for detecting heart muscle actin being optionally lacking fully or partially therefrom and these portions being replaced by others which provide the antibodies with further favorable properties, respectively.

The expression "heart muscle actin" comprises heart muscle actin of any kind and origin as well as fragments thereof. It may originate from human beings or animals. In addition, the heart muscle actin may be present in free or complexed form.

Preferred antibodies of the present invention, namely the monoclonal mouse antibodies Ac1-12.3.1 and Ac1-20.4.2 were deposited with DSMZ located at Mascheroder Weg 1b 38124 Braunschweig, Germany [German-Type Collection of Microorganisms] under numbers DSM ACC 2208 and DSM ACC 2209, respectively, on Mar. 22, 1995 in accordance with the terms of the Budapest Treaty.

Antibodies according to the invention may be produced according to conventional processes. If polyclonal antibodies and monoclonal antibodies, respectively, shall be produced, it will be favorable to immunize animals, particularly rabbits for the former antibodies and mice for the latter antibodies, with an above heart muscle actin and/or fragments thereof, particularly fragments of the N-terminus or C-terminus of heart muscle actin. The expression "fragments thereof" also comprises synthetic peptides which include partial sequences, particularly of the N-terminus or C-terminus, of heart muscle actin. It may also be advantageous to immunize the animals with a mixture consisting of heart muscle actin and/or fragments thereof. Further boosters of the animals may take place with the same heart muscle actin or actins and/or fragments thereof. It is also possible to use other heart muscle actins and/or fragments thereof or a combination of these and the preceding heart muscle actin or actins and/or fragments thereof for booster.

The polyclonal antibodies may then be obtained from the serum of the animals. Spleen cells from the animals are fused with myeloma cells for the monoclonal antibodies.

For the production of synthetic antibodies, e.g. the above obtained monoclonal antibodies may be used as a basis. For this purpose, it is an obvious thing to analyze the antigen binding regions of the monoclonal antibodies and identify the portions necessary and not necessary for the specific heart muscle actin detection. The necessary portions may then be modified and the unnecessary portions may be fully or partially eliminated and be replaced by portions which provide the antibodies with further favorable properties, respectively. Portions can also be modified, eliminated or replaced outside the binding regions of the antibodies. A person skilled in the art is familiar with the fact that particularly the DNA recombination technology is suited for the above measures. He is perfectly familiar with this fact.

Antibodies according to the invention distinguish themselves in that they recognize specifically heart muscle actin and fragments thereof, respectively. Therefore, the antibodies are suitable for a rapid and reliable detection of heart diseases in connection with which heart muscle actin is released. These diseases comprise particularly the cardiac infarct.

The above diseases may be detected by any detection methods, particularly a Western blot, an ELISA, an immunoprecipitation or by immunofluorescence. For this purpose, the antibodies according to the invention may be labeled, if appropriate, or be used in combination with labeled antibodies directed thereagainst. Moreover, the above antibodies may be used in a biosensor process.

According to the invention kits are also provided which contain the above antibodies together with carrier materials and conventional auxiliary agents such as buffers.

BRIEF DESCRIPTION OF THE DRAWING

The figure shows a Western blot in which antibodies according to the invention recognize specifically heart muscle actin over skeletal muscle actin. The respective position of actin is shown on the right-hand margin of the figure by a large arrow each. Lanes 7 and 11, respectively, from (a) show the reaction with heart muscle actin and lanes 7 and 11, respectively, from (b) show the non-reaction with skeletal muscle actin.

The present invention is explained by the below examples.

EXAMPLE 1

Production of Monoclonal Antibodies Against Heart Muscle Actin

Mice of the Balb/c strain were used for immunization. An N-terminal decapeptide of heart muscle actin was used as antigen. This decapeptide contains the following amino acid sequence: DDEETTALVC (SEQ ID No:1). Its N-terminus has an acetyl group, and its C-terminus includes an amide group. The decapeptide was linked as usual with bovine serum albumin (BSA) and Keyhole Limpet Hemocyanin (KLH), respectively.

Immunization and Booster Pattern

100 μg of decapeptide conjugated with BSA emulsified in complete Freund's adjuvant were administered to a mouse.

This was followed by three booster injections using in each case 100 μg decapeptide conjugated in change with KLH (twice) and BSA (once), respectively, the decapeptide having been emulsified in incomplete Freund's adjuvant.

Four days prior to the taking of the spleen cells, the mouse was given intraperitoneally 100 μg of decapeptide conjugated with BSA.

The removed spleen cells were fused with mouse myeloma cells of the known strain X63-Ag8, 653.

Monoclonal antibodies were obtained. Of these, the antibodies referred to as Ac1-12.3.1 and Ac1-20.4.2, respectively, were deposited with DSM under numbers DSM ACC 2208 and DSM ACC 2209, respectively, on Mar. 22, 1995.

EXAMPLE 2

Detection of Heart Muscle Actin by Antibodies According to the Invention

Bovine heart and rabbit muscle were used for the production of protein preparations each. This production was carried out according to a conventional process. The protein preparations were subjected to a polyacrylamide gel electrophoresis and the polypeptides separated in this way were transferred to a nitrocellulose membrane. The latter was then incubated with the above antibodies ACC 2208 and ACC 2209, diluted at 1:10 and 1:50, respectively, at 37° C. for 1 hour. After several wash steps using PBS (0.05% Tween 20) and optionally a wash step using 0.5 M NaCl in PBS, a purchasable anti-mouse antibody coupled to alkaline phosphatase (dilution according to the manufacturer's instructions) was added. After 30 minutes of incubation at 37° C., several wash steps using PBS were carried out and thereafter the alkaline phosphatase detection reaction with developer solution (36 μM 5'-bromo-4-chloro-3-indolylphosphate, 400 μM nitro blue tetrazolium, 100 mM Tris-HCl, pH 9.5, 100 mM NaCl, 5 mM $MgCl_2$) followed at room temperature until bands were visible.

It turned out that the antibodies ACC 2008 and ACC 2209 according to the invention recognize specifically heart muscle actin over skeletal muscle actin. In this connection, the degree of specificity of the antibodies is especially high when the above wash step is carried out with 0.5 m NaCl in PBS.

---

---

What is claimed:

1. An anti-heart muscle actin antibody which binds to heart muscle actin but not skeletal muscle, wherein antigen specificity is determined after a 0.5 M NaCl wash.

2. The antibody of claim 1, wherein said antibody is polyclonal.

3. The antibody of claim 1, wherein said antibody is monoclonal.

4. The antibody according to claim 3, wherein said antibody is deposited with DSM [German-Type Culture Collection of Microorganisms] under ACC 2208.

5. The antibody according to claim 3, wherein said antibody is deposited with DSM under ACC 2209.

6. A process for the production of an antibody according to claim 1, comprising
   (1) immunizing an animal with a peptide consisting of SEQ ID NO:1, and
   (2a) obtaining polyclonal antibodies from the serum of the animal, or
   (2b) obtaining monoclonal antibodies after fusion of spleen cells from the animal with myeloma cells,
   such that an anti-heart muscle actin antibody which binds to heart muscle actin but not skeletal muscle is produced.

7. A method for lesions of heart muscle, said method comprising contacting a biological fluid sample with the antibody of claim 1 such that the presence or absence of heart muscle actin or fragments thereof is detected.

8. The method according to claim 7, wherein the lesion is the result of a cardiac infarct.

9. The method according to claim 7, wherein said method involves a detection step selected from the group consisting of Western blot, an ELISA, an immunofluorescence method, an immunoprecipitation and a biosensor process.

* * * * *